United States Patent [19]
Honda et al.

[11] Patent Number: 5,139,953
[45] Date of Patent: Aug. 18, 1992

[54] ROTARY COLUMN REACTOR

[75] Inventors: Yoshikiko Honda, Sapporo; Morimasa Tanimoto, Sayama; Kaoru Sato, Kawagoe; Shunichi Dosako, Urawa, all of Japan

[73] Assignee: Snow Brand Milk Products Co., Ltd., Hokkaido, Japan

[21] Appl. No.: 569,422

[22] Filed: Aug. 20, 1990

[30] Foreign Application Priority Data

Aug. 29, 1989 [JP] Japan .................... 1-222591

[51] Int. Cl.$^5$ .................................... C12M 1/10
[52] U.S. Cl. ..................... 435/312; 435/313; 435/288
[58] Field of Search ............. 435/288, 312, 313; 210/619, 150, 151

[56] References Cited

U.S. PATENT DOCUMENTS

| | | | |
|---|---|---|---|
| 3,676,074 | 7/1972 | Shibayama | 435/312 |
| 3,905,865 | 9/1975 | McAleer et al. | 435/312 |
| 4,242,450 | 12/1980 | Honda et al. | 435/288 |
| 4,836,918 | 6/1989 | Szikriszt | 210/151 |

Primary Examiner—James C. Housel
Assistant Examiner—Lien Tran
Attorney, Agent, or Firm—Griffin Branigan & Butler

[57] ABSTRACT

A rotary column is rotatably mounted on a hollow shaft having orifices and the shaft is journaled in a reaction vessel. The rotary column has an outer net around the shaft and a space defined by this outer net within the rotary column is divided by partition plates provided with many through-holes into several compartments to be loaded with carriers and immobilized enzymes. The reaction vessel is provided radially outside the compartments with a top cover so that carriers and immobilized enzymes may be easily and evenly loaded into the rotary column. An end surface of the rotary column that is remote from the drive mechanism is provided with a lateral cover. There are provided hydraulic cylinders to tilt the rotary column. Within the reaction vessel, the outer net of the rotary column is provided with rollers adjacent to the lateral cover. Furthermore, there is provided a deaerating pipe within the rotary column and the orifices of the hollow shaft are so dimensioned that, nearer a solution outlet, the diameters of the orifices are larger.

7 Claims, 4 Drawing Sheets

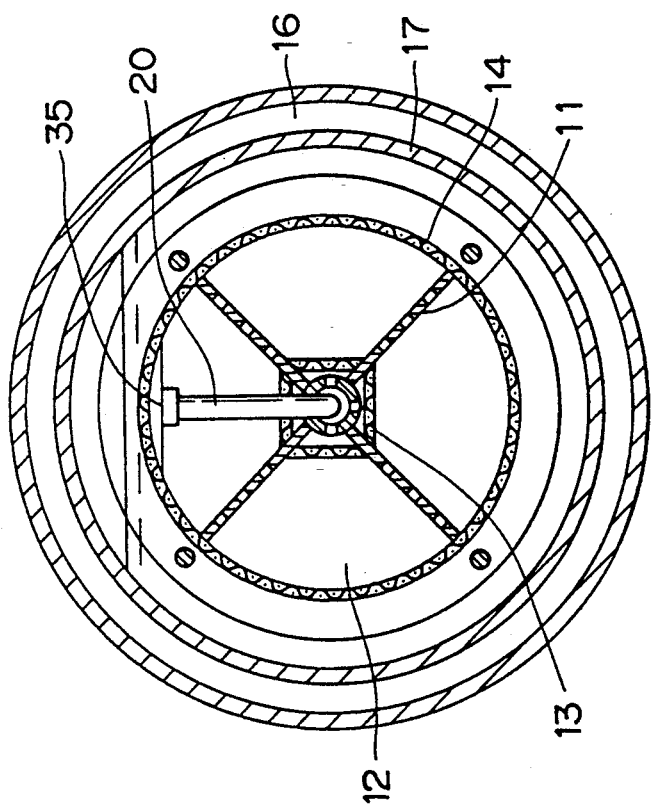

ROTARY COLUMN REACTOR

BACKGROUND OF THE INVENTION

The present invention relates to a rotary column type reactor comprising a rotary column loaded with immobilized enzyme or carriers for specific adsorption of minor constituents or the like contained in a liquid and a reaction vessel housing therein said rotary column.

To collect the minor constituents in a given liquid, it is known to load packed bed or fluidized bed type column or agitator bath with carriers in order to adsorb the minor constituents on said carriers and thereafter to desorb these minor constituents from the carriers for collection thereof.

However, in the packed bed reactor, the carriers tend to become densely packed, resulting in increased pressure loss. Particularly when a large quantity of sample is fed through the packed bed reactor, the reactor of this type makes it difficult to control a flow rate, causes a channeling flow and thereby decreases the adsorption efficiency.

In the agitator bath, on the other hand, a contact efficiency between the carriers and the minor constituents or the like contained in the solution is improved but violent agitation tends to damage the carriers and requires much time and labor for collection of the minor constituents or the like.

Accordingly, members forming part of the present invention proposed, as a system solve such problems and include a reactor comprising a rotary column loaded with immobilized enzyme as disclosed U.S. Pat. No. 4,242,450.

In this reactor of prior art, an outer net surrounding the column must be removed before respective compartments are loaded with carriers, since said compartments are partitioned by plates. When it is desired to use fine carries, meshes of the net surrounding the rotary column must be correspondingly fine. In such case, the net prevents smooth deaeration of the rotary column. When a solution is fed through the rotary column from outer periphery thereof to the centre of the shaft or reversely from the centre of the shaft toward the outer periphery, and particularly when the solution is fed through the rotary column in the former direction at high flow rate, an accumulation of the carries formed around the shaft becomes thicker as the distance from the solution outlet increases and prevents the solution from uniformly flowing among the carriers. As a result, the contact efficiency between the carriers and the solution is lowered.

SUMMARY OF THE INVENTION

It is an object of the invention to provide a rotary column type reactor suitable for adsorption of minor constituents which column permits the carriers to be loaded into the rotary column for even distribution of the carriers throughout the rotary column. The invention also facilitates removal of the carriers out of the rotary column, solves the problem of removing staying air within the column which occurs when it is desired to use fine carriers and correspondingly fine meshes are selected for the net. The invention also allows the solution to flow uniformly among the carriers.

The object set forth above is achieved, in accordance with the invention, by a rotary column type reactor including a rotary column rotatably mounted on a hollow shaft having orifices therearound and journaled in a reaction vessel, said rotary column being adapted to be rotatably driven by a drive mechanism and provided therearound with an outer net so as to define a space divided by partitions into a plurality of compartments to be loaded with carriers, said rotary column type reactor characterized by:

a top cover formed in the reaction vessel radially outside said compartments so that the carriers may be easily and evenly loaded into the rotary column; and said partitions being punched to provide a plurality of through-holes.

In this way, the carriers can be easily and evenly loaded into the rotary column and, therefore, a troublesome operation of loading the carriers into the respective compartments of the rotary column after removal of the outer net can be eliminated. Contact efficiency between solution and carriers is also promoted.

An end surface of the rotary column that is remote from the drive mechanism is preferably provided with a lateral cover to facilitate recovery of the carriers and the rotary column type reactor is preferably provided with lifting means including column supporting legs to further facilitate recovery of the carriers. Additionally, the outer net of the rotary column is preferably provided with rollers within the reaction vessel adjacent the lateral cover to avoid a possibility that the outer net might fall onto the interior surface of the reaction vessel when said lateral cover is opened.

There is preferably provided a deaerating pipe adapted to remove staying air often occurring when a fine mesh net is employed to hold correspondingly fine carriers so that the contact efficiency between the carriers and the solution may be increased and thereby the reaction may be promoted.

The orifices of the rotary column shaft are preferably so dimensioned that, nearer the solution outlet larger the diameters of said orifices. In this way, a back pressure at the proximity of the solution outlet is adjusted to the low level, the flow rate in this region is increased and uneven accumulation of the carriers is avoided.

BRIEF DESCRIPTION OF THE DRAWINGS

The above and other objects of the invention will be seen by reference to the description taken in connection with the accompanying drawings, in which:

FIG. 4 is a sectional view illustrating the deaerating pipe of FIG. 3.

DETAILED DESCRIPTION OF THE INVENTION

Figure 1:
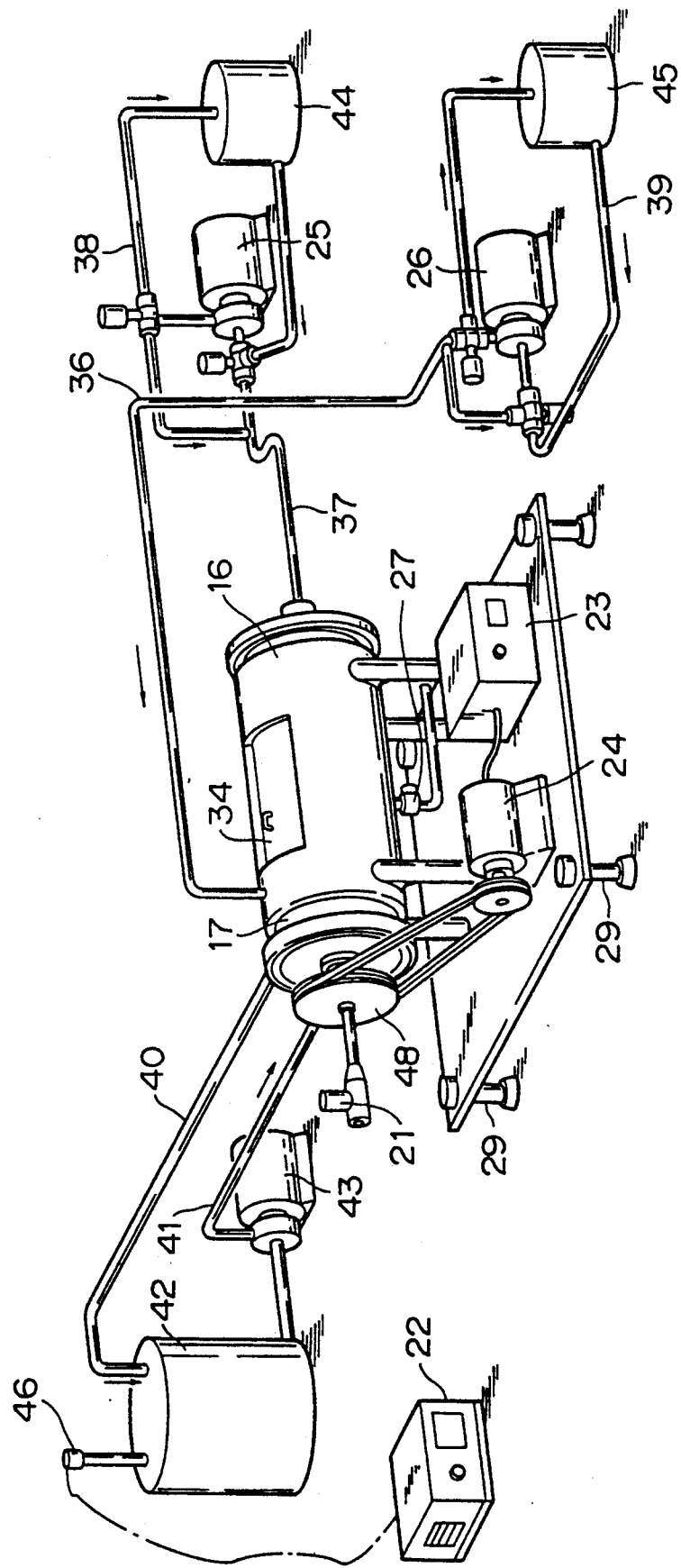
FIG. 1 is a perspective view illustrating an entire rotary column type reactor of the invention.
Figure 2:
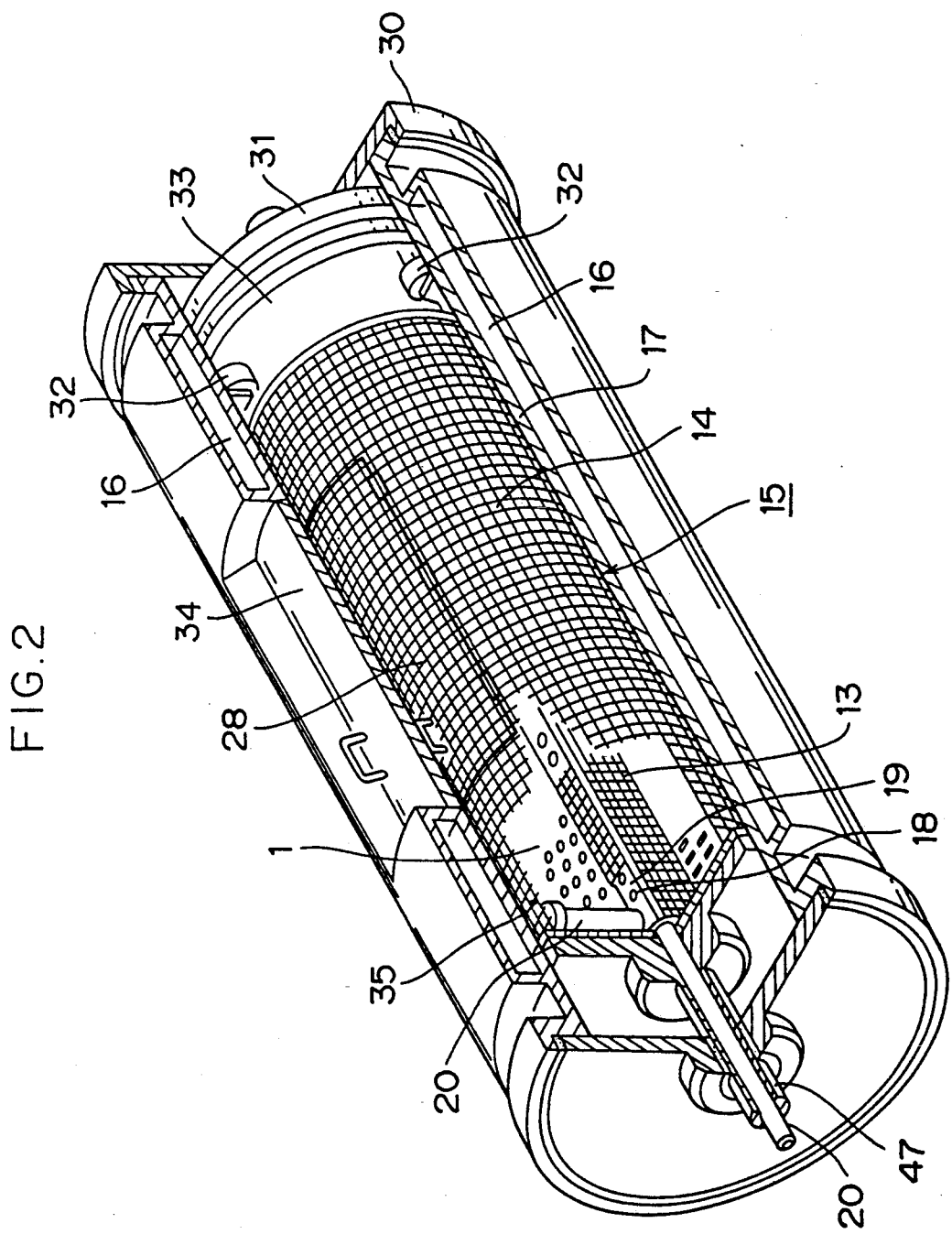
FIG. 2 is a perspective view illustrating, partially in a section, the rotary column of the rotary column type reactor illustrated by FIG. 1.

A specific embodiment of the rotary column type reactor, i.e., the adsorption/desorption apparatus of rotary column type constructed according to the invention will be described in details. FIG. 1 is a perspective view schematically illustrating the rotary column type reactor. Details of the rotary column 15 in FIG. 1 is shown in FIG. 2. As shown, the rotary column 15 is mounted on a hollow shaft 19 having orifices 18 and there is defined between an inner tubular net 13 surrounding said shaft 19 and the outer cylindrical net 14 around the rotary column a space which is, in turn, partitioned by punched metallic plates 11 (see FIG. 4) into several compartments 12 adapted to be loaded with carriers. The shaft 19 of the rotary column is rotatably journaled in a reaction vessel 17 which is provided therearound with a jacket 16 serving to cool the vessel and the shaft 19 is rotationally driven by a variable speed motor 24 (see FIG. 1) which is, in turn, controlled by a speed controller 23. Inflow/outflow of solution through the shaft 19 into/from the reaction vessel 17 of the rotary column is driven by a pump 25 for feed and draw, which is connected to a reservoir 44 via a pipe 38, on one side, and to the shaft 19 via a pipe 37, on the other side. Inflow/outflow of solution into from the reaction vessel 17 of the rotary column through the top thereof is driven by a pump 26 for feed and draw, which is connected to a reservoir 45 via a pipe 39, on one side, and to the top of the reaction vessel 17 via a pipe 36 on the other side.

A stream of cooling water is circulated by a pump 43 from a reservoir 42 through a pipe 41, a cavitity of the jacket 16, a pipe 40 back into the reservoir 42 always under control by a temperature controller 22 cooperating with a sensor 46.

The reaction vessel 17 is provided with a top cover 34 and one of several compartments defined by the punched metallic plates circumferentially partioning the space within the vessel 17 is also provided with a net cover 28 (See FIG. 2). Before the operation, said top cover 34 and net cover 28 are successively opened, then the rotary column is loaded with carriers in gel-state such as agarose, cellulose, silica, chitosan, acrylamide and other macromolecular substances having specific antigen, antibody, heparin, lectin, protein A, protein G and immobilized enzymes thereon, or carriers prepared by processing said gel-state carriers themselves so as to contain functional groups such as a sulfate group and to obtain biological affinity, or commercially available ion-exchange resin of suitable types. Now said top cover 34 and net cover 28 are closed again, and the rotary column 15 is supplied through the orifices 18 of the shaft 19 with liquid such as skimmed milk, milk, whey, blood or liquid medium of microorganism, animals and plants, or solution prepared by subjecting such liquid to spray drying or lyophilization and then dissolving it again into water or suitable buffer solution. After the reaction vessel 17 has been filled with such liquid or solution, the column 15 is rotated. This rotation causes the carriers to move through the holes of the respective punched metallic plates 11 for even distribution throughout the column 15.

Although said holes of the punched metallic plates 11 should have their diameters depending upon a size of the carriers used, it is preferred to select the diameter five to thirty times the average diameter of the carriers which are used.

After the carriers have been evenly distributed throughout the rotary column, any quantity of residual air is removed from the rotary column 15 in a manner as will be described in more details later, and the rotary column 15 is continuously rotated while the pumps 25 and 26 are operated at balanced flow rates through these respective pumps so as to circulate the solution, causing the carriers to adsorb or desorb minor constituents in the solution.

The solution may be fed through the top of the rotary column 15 into the central cavity of the shaft 19 or from said central cavity of the shaft 19 toward the outer periphery of the rotary column 15. No problem occurs in the latter case. In the former case and particular when a flow rate is relatively high, there occurs a problem that an amount of carriers accumulate around the shaft 19. When all the orifices 18 have the same diameters, those more remote from the solution outlet have a thicker accumulation of carriers.

This occurs because of a phenomenon that, the more remote from the solution outlet, the higher the flow rate is and also the amount of carriers carried thereby.

Accordingly, the present invention provides an arrangement such that the orifices have their diameters gradually reduced and thereby a back pressure is adjustably increased at more distant orifices from the solution outlet so as to decrease the volume of flowing solution that would otherwise result in even accumulation of the carriers at this location remote from the solution outlet.

Figure 3:
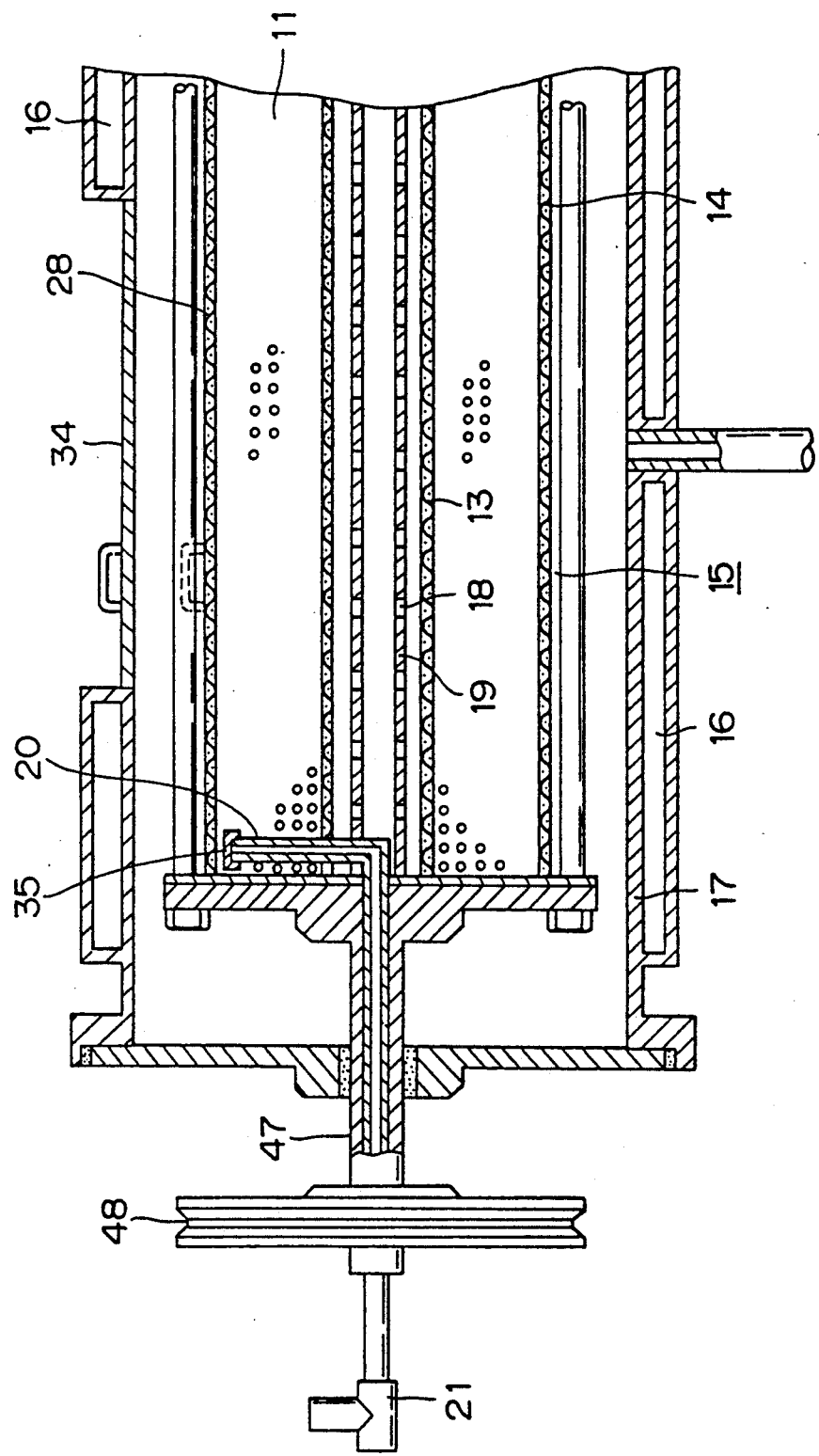
FIG. 3 is a sectional view of the rotary column illustrated by FIG. 2 in the vicinity of the deaerating pipe.

When fine carriers are used, not only the outer cylindrical net 14 but also the inner tubular net 13 of the rotary column 15 should have correspondingly fine meshes, which would necessarily make it difficult to achieve deaeration from the rotary column 15. To solve this problem, in accordance with the invention, a drive shaft 47 including a drive pulley 48 is provided with a deaerating pipe 20, as shown in FIGS. 2, 3 and 4.

Specifically, when the rotary column 15 is initially supplied with the solution, an open end of the deaerating pipe 20 covered with a net cap 35 to prevent the carriers from flowing into said pipe 20 is manually or automatically oriented upward, as seen in FIG. 4, and then a solenoid valve 21 associated with said pipe 20 is opened to the atmosphere. In this manner, any amount of air having stayed within the rotary column can be easily driven out of the reaction vessel 17.

When it is desired to drain the solution off from the rotary column, on the other hand, the open end of the deaerating pipe 20 with the solenoid valve 21 associated therewith kept closed is manually or automatically oriented upward or sideward. Then a drain valve 27 is opened and thereafter said solenoid valve 21 is opened. With a consequence, an air stream flows into the rotary column 15 through the deaerating pipe 20 and a quantity of the solution having stayed within said pipe 20 is driven into the rotary column 15. In this manner, the present invention allows any amount of air having stayed within the rotary column 15 to be easily exhausted.

It should be understood that such deaeration from the rotary column 15 through the deaerating pipe 20 is primarily to increase a contact area between the carriers and the solution. FIG. 4 illustrates a liquid surface within the rotary column 15 and a liquid surface within the reaction vessel 17 occurring when the outer cylindrical net of the rotary column has fine meshes, and deaeration is inadequate. Such situation can be eliminated by deaeration through the pipe 20.

After adsorption or desorption of minor constituents in the subject solution has been performed by the rotary column type reactor, the carriers and the apparatus are washed and sterilized. As for the carriers, those which can withstand washing and sterilizing conditions for the conventional apparatus may be washed and sterilized as they are contained within the apparatus. However, those which can not withstand these conditions must be taken out from the apparatus before they are washed and sterilized. In the former case sometimes it is necessary to take such carriers out from the apparatus.

Accordingly, the rotary column type reactor of the invention is adapted to be tilted as a whole except temperature control system 22, reservoir 42, pump 43 and sensor 46 by activating hydraulic cylinders 29, as will be apparent from FIG. 1. To take the carriers out of the rotary column 15, a lateral outer cover 30 (see FIG. 2) for the reaction vessel 17, which contains therein bearing means, and a lateral inner cover 31 for the rotary column 15 are removed and the reactor is tilted by operation of said hydraulic cylinders 29. Then the top cover 34 of the reaction vessel 17 and the net cover 28 of the rotary column 15 are opened, and through an opening defined by said opened covers 28, 34 an adequate quantity of water or the like is fed into the rotary column 15 so that the carriers are washed away through said lateral opening defined by a lateral outer cover 30 and a lateral inner cover 31, and collected by suitable means such as a net or the like which may be separately provided. The carriers thus collected are separately washed and sterilized for reuse or discarded.

When the rotary column type reactor is tilted, as the laternal outer cover 30 of the vessel which contains therein its own bearings is removed, the rotary column 15 is supported only be bearings provided on the driven side of the rotary column 15. As a result, the bearings provided on the driven side of the column might be overloaded and the outer cylindrical net of the rotary column 15 might fall onto the interior surface of the reactor on the side opposed to said driven side.

To reduce such load, the reaction vessel 17 is provided on its inner surface with a plurality of rollers 32 serving to support the rotary column 15. Those rollers roll in contact with a reinforcement 33 of the rotary column 15 and, during normal operation of the rotary column type reactor also, functions to reduce a load acting upon the bearings.

EXAMPLE 1

The net cover 28 of a 5 l rotary column 15 arranged within a 20 l vessel having a jacket and covered therearound with a 200 mesh net was opened, and 800 cc of agarose gel immobilized monoclonal anti-bovine lactophelin was loaded as carriers into the rotary column 15. The maximum amount of lactophelin adsorption on this type of carriers was 2.5 g/ml (carriers).

Then non-sterilized whey (100 l) was fed through the orifices 18 of the shaft 19 into the rotary column at a flow rate of 180 l/h until the rotary column 15 was completely immersed in the non-sterilized whey. The rotary column 15 was rotated so as to orient the open end of the deaerating pipe 20 upward and then the solenoid valve 21 was opened to deaerate the column 15. After the proper deaeration was determined, the solenoid valve 21 was closed again, an additional quantity of whey was supplied into the rotary column 15 while the latter is rotated at a speed of 18 rpm, and thereby lactophelin contained in whey was adsorbed on the carriers. After the whole quantity of whey had been supplied, the carriers were washed twice with 20 l of 0.5M saline solution, then twice with phosphoric acid buffer solution then with, 20 l of 0.2M acetic acid buffer solution, and finally 2.16 g of lactophelin was recovered from the carriers on which said lactophelin had been adsorbed. Lactophelin thus recovered presented a purity of 98%.

EXAMPLE 2

The net cover 28 of the 2.6 l rotary column arranged within the 7 l vessel and covered with a 200 mesh net was opened and 1.3 l of sulfated chitosan beads were loaded into the rotary column. Then the sulfated chitosan beads were washed and sterilized with alkali solution and warm water.

The non-sterilized skimmed milk was fed through the orifices 18 of the shaft 19 into the rotary column 15 until the rotary column 15 was completely immersed in the non-sterilized skimmed milk.

With the rotary column 15 thus immersed in the non-sterilized skimmed milk, the rotary column 15 was rotated so as to orient the open end of the deaerating pipe 20 upward and then the solenoid valve 21 was opened to deaerate the rotary column 15. Thereafter the rotary column 15 was rotated at a speed of 18 rpm. Then 200 l of skimmed milk was fed at a flow rate of 200 l/h outwardly through the orifices 18 of the shaft 19 or reversely from outside the column into the shaft 19 and thus lactophelin contained in the skimmed milk was adsorbed on the sulfated chitosan beads.

After the whole quantity of skimmed milk had been fed into the column 15, 70 l of warm water at a temperature of 30° to 35° C. and 0.15M saline solution were fed in the same direction as said skimmed milk had been fed while the rotary column 15 was rotated to wash the carriers. After the carriers had been washed in this manner, 1M saline solution was fed into the rotary column in the same direction as that for said skimmed milk to collect lactophelin from the carriers on which said lactophelin had been adsorbed. Recovery amount of lactophelin depended on the circulating or feeding direction, i.e., 4.6 g of lactophelin was recovered when the skimmed milk had been fed radially from the center toward the outer periphery of the rotary column 15 and 5.6 g was recovered when the skimmed milk had been fed in the reverse direction. In the latter case, the time taken for desorption of lactophelin from the carriers was reduced by 36%. A purity of the recovered lactophelin was 90%.

EXAMPLE 3

After mouse hybridoma had been cultivated for a month in DME medium containing 5% fetal calf serum, 30 l of culture supernatant liquid was obtained by centrifugation. This supernatant liquid was loaded into the rotary column 15 previously filled with Sephadex G-25 and desorbed by using pH 5.3 citric acid buffer solution. Then, about 300 l of this void fraction was fed through the rotary column (of the same type as was used in Example 2) filled with 1.8 l of S cephalose ion-exchange resin in the manner as has been explained in Example 2.

Upon completion of feeding the liquid, washing with warm water was performed and then 20 l of citric acid buffer solution containing 140 mM saline was fed to desorb the mouse monoclonal antibody. The amount of recovery thereof was 220 mg when the circulation was made from the centre toward the outer periphery of the rotary column and 345 mg when the feeding was made in the reverse direction. In both cases, a purity was approximately 75%.

EXAMPLE 4

The 500 ml rotary column arranged within the 600 ml vessel was filled with 200 ml of heparin cephalose as carriers and equilibrated with 0.027 M McIlvaine's buffer solution (pH 7.2) containing 0.05 M sodium chloride.

80 ml of human serum positive to HBs antigen of hepatitis B virus was diluted by said buffer solution to obtain 600 ml of solution which was, in turn, circulated through the rotary column at a flow rate of 30 l/h for 30 minutes.

Upon completion of such circulation, an adequate quantity of said buffer solution was used to perform washing, and then 600 ml of 0.027 M McIlvaine's buffer solution (pH 7.2) containing 0.6 M sodium chloride was fed into the rotary column to desorb HBs antigen which had been adsorbed on the gel. Recovery percentage of this HBs antigen from the serum was 94.2%. Purity of the recovered protein (amount of antigen/protein) was improved 14.3 times.

While the invention has been particularly shown and described with reference to preferred embodiment thereof, it will be understood by those skilled in the art that the foregoing and other changes in form and detail can be made therein without departing from the spirit and scope of the invention.

What is claimed is:

1. In a rotary column reactor including a rotary column rotatably mounted on a hollow shaft having orifices therearound and said shaft being journaled in a reaction vessel, said rotary column being constructed and arranged so as to be rotatably driven by a drive mechanism and said column being provided with an outer net extending circumferentially along said shaft so as to define a space between said shaft and said net, which space is axially divided by a plurality of axially disposed partition plates extending along the axis of said shaft into a plurality of axial compartments to be loaded with carriers, the improvement comprising:
   a top cover formed in the reaction vessel radially outside said compartments so that the carriers may be easily and evenly loaded into the rotary column; and
   said partition plates being punched to provide a plurality of transverse through-holes having a diameter from 5 to 30 times the average diameter of the carriers to be used.

2. A rotary column reactor as recited in claim 1, wherein an end surface of the rotary column that is remote from the drive mechanism is provided with a lateral cover.

3. A rotary column reactor as recited in claim 2, wherein the outer net of the rotary column is provided with rollers.

4. A rotary column reactor as recited in claim 3, wherein said rollers are provided on the outer net of the rotary column within the reaction vessel adjacent the lateral cover.

5. A rotary column reactor as recited in claim 1, wherein there are provided means to tilt the rotary column.

6. A rotary column reactor as recited in claim 1 wherein a deaerating pipe is provided within the hollow shaft of the rotary column.

7. A rotary column reactor as recited in claim 1 wherein said orifices of the hollow shaft being so dimensioned that, nearer a solution outlet for the reactor column, the diameters of said orifices are larger.

* * * * *